United States Patent [19]

Gavras et al.

[11] Patent Number: 4,574,079
[45] Date of Patent: Mar. 4, 1986

[54] RADIOLABELED ANGIOTENSIN CONVERTING ENZYME INHIBITORS FOR RADIOLABELING MAMMALIAN ORGAN SITES

[76] Inventors: Haralambos P. Gavras, 11 Coolidge Rd., Wayland, Mass. 01778; James W. Ryan, 3420 Poinciana Ave., Miami, Fla. 33133; Alfred Chung, 8781 SW. 87th Ave., Miami, Fla. 33125

[21] Appl. No.: 498,736

[22] Filed: May 27, 1983

[51] Int. Cl.$^4$ ............... A61K 43/00; A61K 49/00; A61K 49/02; C07C 103/52
[52] U.S. Cl. ............... 424/1.1; 260/112.5 R; 424/9
[58] Field of Search ............... 424/1.1, 9; 260/112.5 R

[56] References Cited

U.S. PATENT DOCUMENTS

| | | | |
|---|---|---|---|
| 4,201,012 | 5/1980 | Strecker et al. | 424/1 |
| 4,243,652 | 1/1981 | Francis et al. | 424/1 |
| 4,272,503 | 6/1981 | Camin et al. | 424/1 |
| 4,279,887 | 7/1981 | Baldwin | 424/1 |
| 4,280,991 | 7/1981 | Birch | 424/1 |
| 4,284,619 | 8/1981 | Lin | 424/1 |
| 4,287,362 | 9/1981 | Yokoyama | 424/1 |
| 4,293,537 | 10/1981 | Wong | 424/1 |
| 4,301,140 | 11/1981 | Frank et al. | 424/1 |
| 4,305,922 | 12/1981 | Rhodes | 424/1 |
| 4,307,072 | 12/1981 | Smith | 424/1 |
| 4,307,182 | 12/1981 | Dalzell et al. | 424/1 |
| 4,308,202 | 12/1981 | Fujii et al. | 424/1 |
| 4,308,249 | 12/1981 | Frank et al. | 424/1 |
| 4,310,505 | 1/1982 | Baldeschwieler et al. | 424/1 |
| 4,310,506 | 1/1982 | Baldeschwieler et al. | 424/1 |

(List continued on next page.)

FOREIGN PATENT DOCUMENTS 0048159 3/1982 European Pat. Off. ............ 424/1

OTHER PUBLICATIONS

Wieland, from *Receptor-Binding Radiotracers*, Ed. Eckelman, CRC Press, Inc., Boca Raton, Fl. (1982) pp. 127–146.

Beierwaltes et al, from *Principles of Radiopharmacology*, vol. II, Ed. Colombetti, CRC Press, Inc., Boca Raton, Fla. (1979) pp. 41–57.

(List continued on next page.)

*Primary Examiner*—Christine M. Nucker
*Attorney, Agent, or Firm*—Memel Jacobs Pierno, Gersh & Ellsworth

[57] ABSTRACT

Radiolabeled angiotensin converting enzyme inhibitors having the general formula:

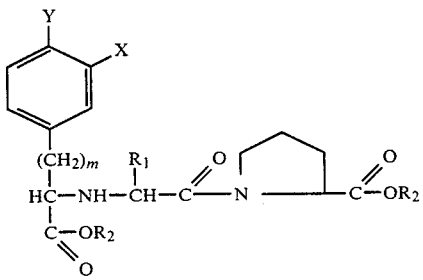

wherein
X is a radiolabeling substituent, preferably a radiolabeling halogen substituent such as $^{123}I$, $^{125}I$, $^{131}I$, $^{75}Br$ or $^{77}Br$,
Y is hydroxy, alkoxy containing from 1 to 6 carbon atoms, phenoxy, benzyloxy, or amino,
$R_1$ is hydrogen or methyl,
$R_2$ is hydrogen, an ester moiety hydrolyzable under mammalian in vivo conditions, such as alkyl of 1 or 2 carbon atoms, phenyl or benzyl, or an ionically bonded anion of a physiologically acceptable non-toxic salt, and
m is an integer of from 1 to 6, are useful as in vivo radioimaging compounds for mammalian sites.

10 Claims, 2 Drawing Figures

U.S. PATENT DOCUMENTS

| | | |
|---|---|---|
| 4,313,926 | 2/1982 | Samochocka ............................ 424/1 |
| 4,313,928 | 2/1982 | Kato et al. ............................... 424/1 |
| 4,316,883 | 2/1982 | Schrijuer .................................. 424/1 |
| 4,318,898 | 3/1982 | Molter et al. ............................ 424/1 |
| 4,323,546 | 4/1982 | Crockford et al. ...................... 424/1 |
| 4,337,240 | 6/1982 | Saklad ..................................... 424/1 |
| 4,340,662 | 7/1982 | Oushinsky ............................... 424/1 |
| 4,342,740 | 8/1982 | Nara ........................................ 424/1 |
| 4,350,674 | 9/1982 | Molter et al. ............................ 424/1 |
| 4,360,509 | 11/1982 | Goedemans ............................. 424/1 |
| 4,363,793 | 12/1982 | Blau et al. ................................ 424/1 |
| 4,364,920 | 12/1982 | Winchell ................................. 424/1 |
| 4,374,829 | 2/1983 | Harris et al. ......................... 424/177 |

OTHER PUBLICATIONS

Kripilani et al, "Disposition of Captopril in Normal Subjects", Clin. Pharmacol. Ther., 27, 636 (1980).

Beierwaltes et al, "Localization of Labelled Enzyme Inhibitors in the Adrenal Gland", *J. Nucl. Med.*, 17, 998 (1976).

Beierwaltes et al, "Imaging the Adrenal Glands with Radiolabelled Inhibitors of Enzymes", *J. Nucl. Med.*, 19, 200 (1978).

Beierwaltes et al, "Adrenal Imaging Agents, Rationale, Synthesis, Formulation and Metabolism", *Seminars in Nuclear Medicine*, 8, 5 (1978).

Johns, "$^{131}$I-3'-Iodoaminopterin: A Gamma-Labelled Active Site Directed Enzyme Inhibitor", *J. Nucl. Med.*, 9, 530 (1968).

Houben Weyl, *Methoden de Organischen Chem.*, 15, Part II, pp. 1 et seq. (1974).

Houben Weyl, *Methoden de Organischen Chemie*, vol. 15, Part 1, pp. 376–380.

Friedman et al, "The Use of Radiobrominated p–Bromospiroperidol for γ-Ray Imaging of Dopamine Receptors", *Int. J. Nucl. Med. & Biol.*, 9, 57 (1982).

Chevillard et al, "Distribution of Angiotensin–Converting Enzyme Activity in Specific Areas of the Rat Brain Stem", *J. Neurochem.*, 38, 282 (1982).

Rohatgi et al, "Significance of Serum Angiotensin Converting Enzyme and Gallium Scan in Noninvasive Diagnosis of Sarcoidosis", *Eur. J. Resp. Dis.*, 62, 223 (1980).

Gupta et al, "Gallium 67 Citrate Scanning and Serum Angiotensin Converting Enzyme Levels in Sarcoidosis", *Radiology*, 144, 895 (1982).

Sisson et al, "Scintigraphic Localization of Pheochromocytoma", *NEJM*, 305, 12 (1981).

Knapp et al, "Potential Pancreatic Imaging Agents, Tellurium-123 m Labeled DL-α-Amino-γ-(Phenyltelluro)Butyric Acid", *J. Med. Chem.*, 24, 794 (1981).

Mills, "Rapid Synthesis of $^{123}$I-Labeled Iodinated Contrast Media by 'Kit'-Type Labeling Procedure", *Int. J. Appl. Radiat. Isotop.*, 33, 467 (1982).

Hawkins et al., "A Rapid Quantitative Method for the Production of $^{123}$I-Hippuran", *J. Labelled Compounds and Radiopharmaceuticals*, 18, 126 (1981).

Hawkins et al, "A Rapid Quantitative Method for the Preparation of $^{123}$I-Iodo-Hippuric Acid", *Eur. J. Nucl. Med.*, 7, 58 (1982).

Scheinbert et al, "Tumor Imaging with Radioactive Metal Chelates Conjugated to Monoclonal Antibodies", *Science*, 215, 1511 (1982).

Hasegawa et al, "The Synthesis of SQ-14225-$^{14}$C[N-[(-s)-2-Methyl-3-Mercaptopropanoyl-1-$^{14}$C]", *J. Labelled. Comp. and Radiopharmaceuticals*, 18, 643 (1980).

RADIOLABELED ANGIOTENSIN CONVERTING ENZYME INHIBITORS FOR RADIOLABELING MAMMALIAN ORGAN SITES

FIELD OF THE INVENTION

This invention relates to radiopharmaceuticals useful for the radioimaging of mammalian sites, including certain organs. More particularly, this invention relates to a particular class of radiolabeled angiotensin converting enzyme inhibitors and to their use as radiopharmaceuticals for the radioimaging of mammalian sites, including certain organs.

BACKGROUND OF THE INVENTION

Angiotensin converting enzyme (peptidyl-dipeptide hydrolase, a dipeptide-liberating exopeptidase hereinafter referred to as ACE) converts the physiologically inactive decapeptide angiotensin I, which has the sequence:

AspArgValTyrIleHisProPheHisLeu (wherein Asp=L-aspartic acid, Arg=L-arginine, Val=L-valine, Tyr=L-tyrosine, Ile=L-isoleucine, His=L-histidine, Pro=L-proline, Phe=L-phenylalanine and Leu=L-leucine) to the most potent naturally occurring pressor substance known—the octapeptide angiotensin II—by catalyzing the hydrolysis of the penultimate peptide bond to effect removal of the carboxyl-terminal HisLeu. ACE also acts as a catalyst for the hydrolysis of the penultimate peptide bond in a variety of acylated tripeptides and larger polypeptides which have an unblocked α-carboxyl group.

In a second series of reactions, ACE inactivates the powerful vasodepressor bradykinin by catalyzing the hydrolytic release of one or more carboxyl-terminal dipeptides from this nonapeptide.

ACE is not distributed uniformly throughout mammals, whether humans or animals, but instead is concentrated at sites of a few cell types within a relatively small number of tissues. Specifically, the presence of ACE in mammals appears to be largely restricted to endothelial cells of the vascular tree (including the lymphatic system), the brush border epithelium of the kidneys and gut, the testicles, seminal plasma and blood plasma. ACE activity has also been found in the brain, particularly in the brain stem. In some disease states, ACE may also be concentrated in granulomas characteristic of Boeck's sarcoid and in the spleen tissue of patients affected by Gaucher's disease.

In recent years, a number of chemical compounds which act in vivo as enzyme inhibitors, including ones which act as ACE inhibitors, have been synthesized. Certain of these enzyme inhibitors, again including one ACE inhibitor known to the present inventors, have been labeled with radioisotopes [articles by Kripalani et al, *Clin. Pharmacol. Ther.*, 27, 636 (1980) and Wong et al, *Pharmacologist*, 21, 155 (1979) describe the synthesis of $^{35}$S-3-mercapto-2-D-methylpropanoyl-L-proline ($^{35}$S-captopril) and $^{14}$C-labeled captopril, respectively, for the purpose of studying the disposition of captopril in humans and animals]. And certain of the thus-labeled enzyme inhibitors (although, to the present inventors' knowledge, no ACE inhibitors) have been used to radioimage mammalian sites.

A series of papers by Beierwaltes et al, *J. Nucl. Med.*, 17, 998–1002 (1976); *J. Nucl. Med.*, 19, 200–203 (1978); *Seminars in Nuclear Medicine*, 8, 5–21 (1978), report on experiments using radiolabeled enzyme inhibitors in attempts to image the adrenal glands in rats, dogs and humans. These studies showed that in some cases, radiolabeling one inhibitor for an adrenocortical enzyme enhanced its uptake by the adrenal cortex, while radiolabeling another adrenocortical enzyme inhibitor markedly decreased its uptake by the target organ. It thus appears from these studies that one cannot know in advance how labeling with a radioisotope will affect tissue uptake and, consequently, the usefulness of an enzyme inhibitor as a radiopharmaceutical for imaging mammalian sites.

Johns et al, *J. Nucl. Med.*, 9, 530–535 (1968) reported on the use of 3'-$^{135}$iodoaminopterin, an inhibitor of dihydrofolate reductase, to radioimage organs where this enzyme is found.

Various radiopharmaceuticals said to be useful for radioimaging mammalian sites are disclosed in U.S. Pat. Nos. 4,243,562; 4,243,652; 4,279,887; 4,316,883; 4,318,898; 4,323,546; 4,350,674 and 4,360,509.

BRIEF DESCRIPTION OF THE INVENTION

We have now discovered that radiolabeled ACE inhibitors having the general formula:

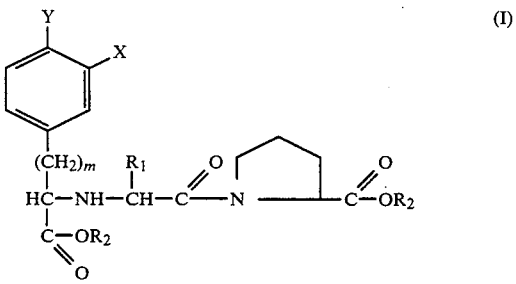

wherein

X is a radiolabeling substituent, preferably a radiolabeling halogen substituent such as $^{123}$I, $^{125}$I, $^{131}$I, $^{75}$Br or $^{77}$Br, Y is hydroxy, alkoxy containing from 1 to 6 carbon atoms, phenoxy, benzyloxy or amino, $R_1$ is hydrogen or methyl, $R_2$ is hydrogen, an ester moiety hydrolyzable under mammalian in vivo conditions, such as alkyl of 1 or 2 carbon atoms, phenyl or benzyl, or an ionically bonded anion of a physiologically acceptable nontoxic salt, and m is an integer of from 1 to 6, are useful as in vivo radioimaging compounds for mammalian sites, including human and mammalian organs, particularly those where ACE is present in abundance. These radiolabeled compounds react with ACE in vivo to form tight complexes of finite half life, and permit clear and detailed imaging of the target organs by means of a gamma camera, sodium iodide crystal probes or scanners, a standard ANGER camera (Searle), or any other suitable means known to those skilled in the art.

A particularly preferred group of radiolabeled ACE inhibitors coming within the above general formula I are those having the formula:

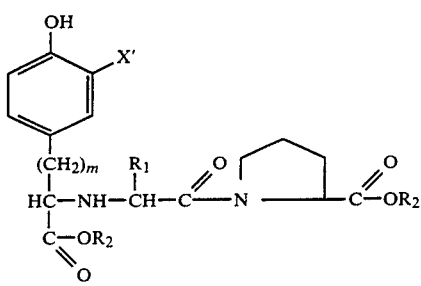

wherein X' is a radiolabeling iodine substituent and $R_1$, $R_2$ and m are as described for formula I above. Included among these particularly preferred compounds are the radioiodinated derivatives of N-[L-1-carboxy-2-(4-hydroxyphenyl)ethyl]-Ala-L-Pro (Ala being the symbol for an alanyl moiety) represented by the formula:

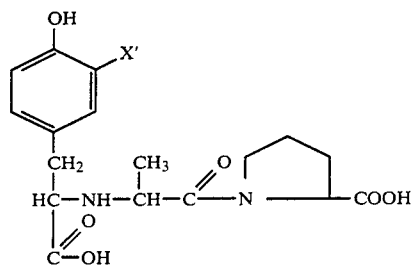

wherein X' is as described for formula II above, particularly $^{123}I$ or $^{131}I$.

DETAILED DESCRIPTION OF THE INVENTION

The starting materials for the preparation of the radiolabeled ACE inhibitors of the present invention, i.e., compounds having the general formula:

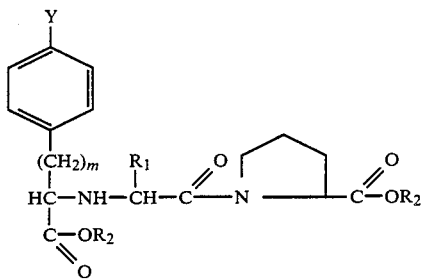

wherein Y, $R_1$, $R_2$ and m are as described for formula I above, are prepared as described in Ryan and Chung European Laid Open Application No. 0048159, which was laid open for public inspection on May 12, 1982.

One method described in the aforementioned European Laid Open Application for producing compounds of formula IV above involves, briefly, coupling an α-keto carboxylic acid (present in excess, as will be any α-keto carboxylic acid used in the procedures described herein) having the formula

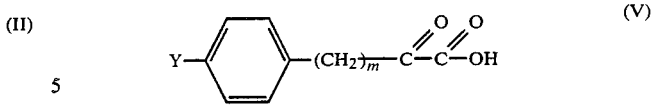

wherein Y and m are as described for formula I above, with benzyl alcohol, using the carbodiimide coupling method in an anhydrous organic solvent such as tetrahydrofuran or dimethylformamide at a temperature of about −50° C., to produce a compound having the formula:

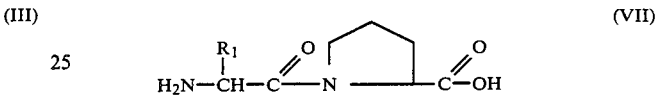

This product is then reacted with a compound having the formula:

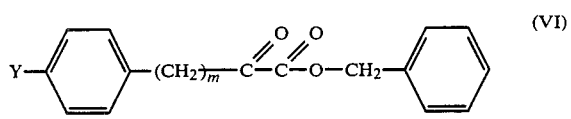

wherein $R_1$ is as described for formula I above [and see U.S. Pat. No. 4,374,829, issued Feb. 22, 1983 to Harris et al, beginning at column 5, line 1 "Method I, Route 1 ($R^2=H$)"] to yield:

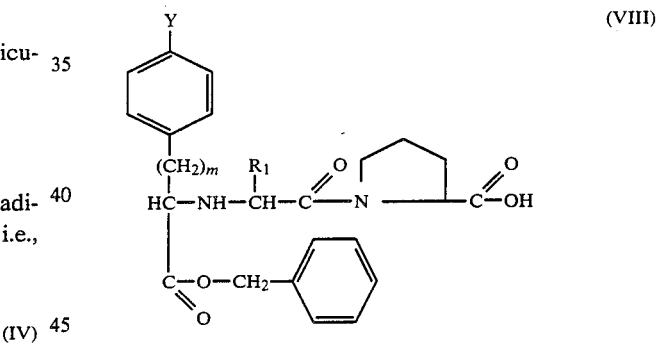

Reacting this compound with 1M potassium hydroxide in ethanol at room temperature for about 1 hour gives the desired compounds:

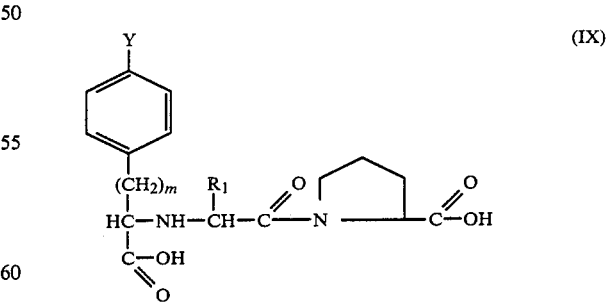

In another method described in the aforementioned European Laid Open Application for making the compounds of formula IV above, an excess of a suitable α-keto-carboxylic acid of formula V above, in the form of its ethyl ester, is coupled to an amino acid having the formula:

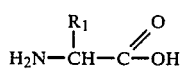

to give:

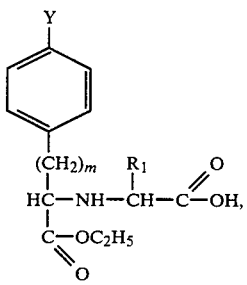

which is then coupled to the benzyl ester of L-proline to give the desired compounds. Alternatively, the amino acid of formula X above, with its amino group protected by a carbobenzyloxy group, can first be coupled to L-proline, by the acid chloride method, and then deprotected using anhydrous trifluoroacetic acid, to give:

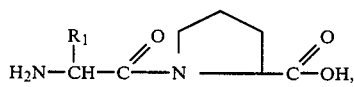

which can then be coupled to an α-ketocarboxylic acid of formula V above to give the desired compounds.

A general method described in the aforementioned European Laid Open Application for producing the compounds of formula IV above involves coupling a suitable α-ketocarboxylic acid, present in excess, which has the formula:

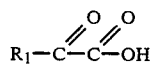

with the benzyl ester of L-proline, using a conventional coupling agent such as dicyclohexylcarbodiimide or diphenylphosphorylazide in dimethylformamide at about −50° C., to give:

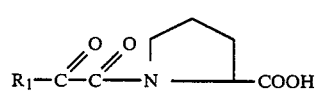

This product is in turn coupled, in the presence of a reducing agent such as sodium cyanoborohydride in solution in an aqueous organic solvent such as chloroform or dichloromethane, with a compound having the formula:

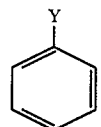

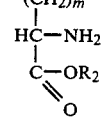

to give the desired compounds. Alternatively, the α-ketocarboxylic acid of formula XIII above can first be coupled with the compound of formula XV above, then protected by means of the ethyl ester, and the resulting product:

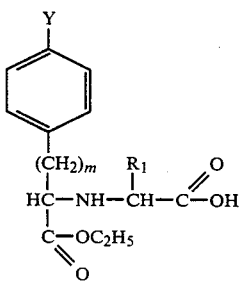

can then be coupled with L-proline.

A review of suitable coupling methods useful in preparing the starting materials of formula IV above—the mixed anhydride, dicylohexylcarbodiimide, diphenylphosphorylazide, symmetrical anhydride, acid chloride, active ester, Woodward reagent K and like methods—is found in *Methoden der Organischen Chemie* (Houben-Weyl), Vol. 15, part II, pp. 1 et seq. (1974). As is well known in the art, conventional protecting groups—ethyl, benzyl, t-butyloxycarbonyl (Boc), carbobenzyloxy (Cbo), and the like—may be introduced at appropriate stages to block or protect reactive groups, especially carboxyl or amido groups, and will then be removed as desired by conventional means—treatment with trifluoroacetic acid and anisole, for example—as described in *Methoden der Organischen Chemie* (Houben-Weyl), Vol. 15, part I, pp. 376 et seq. (1974).

Radiolabeling of the starting materials of formula IV above to produce the radiolabeled ACE inhibitors of the present invention will also be carried out using well known methods. Thus, for example, radiolabeling with radioactive iodine isotopes—$^{123}$I, $^{125}$I or $^{131}$I—or with radioactive bromine iostopes—$^{75}$Br or $^{77}$Br—can be carried out using such methods as the chloramine T and Iodogen methods.

Among the specific uses for the radiolabeled ACE inhibitors of the present invention are the following:

In the assessment of:
myocardial perfusion (e.g., to estimate infarction size),
sites of occult hemorrhage,
sites of arterio-venous shunting,
testicular function and testicular tumors,
skin blood flow (perfusion) and skin lesions,
patency of by-pass grafts (coronary and peripheral),
allograft rejection,
brain perfusion, ocular perfusion.

To assist in the diagnosis of:
esophageal varices,
sarcoid uveitis,
Gaucher's disease.

To assist in the assessment and diagnosis of:
cavernous hemangiomas,
edema and effusions: pulmonary, pleural and abdominal.

In the visualization of:
lymphatics and regional lymph nodes,
peripheral arteries.

In the identification or detection of:
tumors or granolomas (e.g. sarcoid) enriched in ACE,
leaking Berry aneurysms.

In the differential diagnosis of cardiac hypertrophy vs. cardiac dilatation.
In:
autoradiography of blood vessels of the hands and feet,
phlebograms (for venous thrombosis).

The radiolabeled ACE inhibitors of the present invention can be administered by injection, for example in saline solution, into a blood vessel in the mammal whose organ(s) are to be radioimaged at a dosage within the range of from about 0.01 mg/kg of body weight to about 15 mg/kg of body weight, and preferably from about 0.05 mg/kg of body weight to about 5 mg/kg of body weight, the total radioactivity from such a dose ordinarily being less than about 100 $\mu$Ci, and preferably less than about 75 $\mu$Ci, particularly when radioimaging human organs or other body sites.

Figure 1:
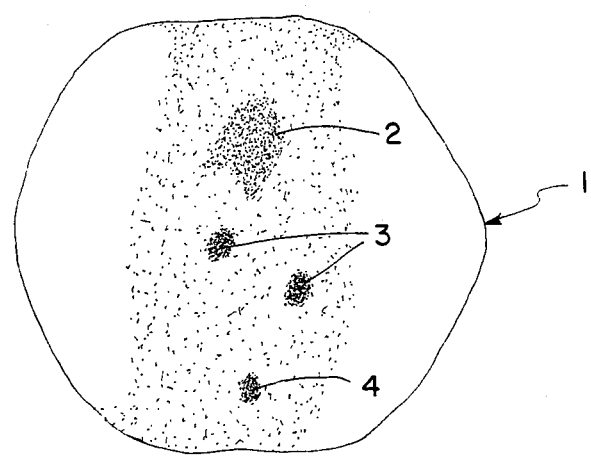
FIG. 1 is a representation of an anterior-posterior view of the scan described in Example II.

In order that those skilled in the art can more fully understand the present invention, the following examples are set forth. These examples are given solely for purposes of illustration, and should not be considered as expressing limitations unless so set forth in the appended claims.

PREPARATION A

Synthesis of
N-[L-1-methoxycarbonyl-2-(4-benzyloxyphenyl)ethyl]-Ala-L-Pro methyl ester The hydrochloride salt of O-benzyl-L-tyrosine methyl ester (2 mmols) in 7 ml of absolute ethanol plus 0.25 ml of water was mixed with 2 mmols of sodium bicarbonate. To this solution were added 10 mmols of N-pyruvoyl-L-proline methyl ester and 3.2 g of powdered M-2385 molecular sieve (Sigma Chemical Company, St. Louis, Mo.). The resulting mixture was stirred for 30 minutes, following which 130 mg of sodium cyanoborohydride in 2.5 ml of absolute ethanol was added dropwise, with stirring, over a period of 4 hours at room temperature (about 25° C.). The resulting mixture was then stirred overnight at room temperature. Next, the molecular sieves were removed by filtration and the precipitate was washed with a small amount of ethanol. The solvent from the combined filtrates was removed under reduced pressure to yield an oil. Part (0.38 g) of the crude product was purified by partition chromatography (1.2×98 cm column) with Sephadex G-25 equilibrated with butanol/acetic acid/$H_2O$ (4:1:5 by volume). The product (277 mg) was eluted with the upper phase, and the recovered material was further purified on Sephadex LH-20 (2.2×100 cm column), equilibrated and developed with tetrahydrofuran/isopropanol (3:7 by volume).

PREPARATION B

Synthesis of
N-[L-1-carboxy-2-(4-benzyloxyphenyl)ethyl]-Ala-L-Pro

330 Mg of N-[L-1-methoxycarbonyl-2-(4-benzyloxyphenyl)ethyl]-Ala-L-Pro methyl ester, synthesized as described in Preparation A above, was saponified in 1.5 ml of 1M potassium hydroxide in methanol at room temperature for 1 hour. The crude product obtained was partially purified by means of the partition chromatography step described in Preparation A above, using Sephadex G-25, and then chromatographed on Dowex 50W-x8 (1.2×48 cm column) eluted with 2% pyridine to give an apparently pure product.

PREPARATION C

Synthesis of
N-[L-1-carboxy-2-(4-hydroxyphenyl)ethyl]-Ala-L-Pro

Ten mg. of N-[L-1-carboxy-2-(4-benzyloxyphenyl)ethyl]-Ala-L-Pro, synthesized as described in Preparation B above, in 1 ml of methanol was hydrogenated for 5 hours at room temperature with hydrogen gas at 10 psi, using 10 mg of 10% palladium on carbon as catalyst. The catalyst was removed by filtration, the the solvent was removed with a rotary evaporator. The material was further purified by chromatography on Sephadex G-10 (1.2×99 cm), equilibrated and developed with 2% pyridine. The desired product was obtained in a yield of 5.8 mg.

EXAMPLE I

Radiolabeling of
N-[L-1-carboxy-2-(4-hydroxyphenyl)ethyl]-Ala-L-Pro

A. Synthesis of
N-[L-1-carboxy-2-(4-hydroxy-3-$^{125}$iodophenyl)ethyl]-Ala-L-Pro A freshly prepared solution of 0.95 mg (2.2 $\mu$mol) of Iodogen (Pierce Chemical Co.) in 1.0 ml of chloroform was coated onto the interior surface of a 12×75 mm polypropylene tube containing the Iodogen solution. The tube was rotated while removing the solvent with a stream of dry nitrogen gas. Any flaking material formed during this step was removed.

A solution of 1.02 mg (2 $\mu$mol) of N-[L-1-carboxy-2-(4-hydroxyphenyl)ethyl]-Ala-L-Pro, synthesized as described in Preparation C above, and 37 mg of sodium iodide containing 1 $\mu$Ci of sodium $^{125}$iodide in sodium hydroxide (as supplied by Amersham Corp.), together with 1 ml of 0.05M sodium phosphate buffer at pH 7.4, was added to the polypropylene tube containing precipitated Iodogen. The resulting mixture was incubated in an ice bath at 0° C. for 10–15 minutes with occasional mixing, following which the radioiodinated product was separated from the Iodogen by decanting the phosphate buffered reaction solution from the Iodogen-coated tube.

Thin layer chromatography (on Tech silica gel, System: butanol:pyridine:acetic acid:water 15:10:3:12, $R_f$ 0.485) showed less than 4% of unreacted sodium iodide (Note: $R_f$ for sodium iodide is 0.63; $R_f$ for starting material from Preparation C is 0.40).

B. Synthesis of N-[L-1-carboxy-2-(4-hydroxy-3-$^{123}$iodophenyl)ethyl]-ala-L-Pro The procedure of section A above was repeated using 1.02 mg of N-[L-1-carboxy-2-(4-hydroxyphenyl)ethyl]-Ala-L-Pro and 37 mg of sodium iodide containing 1 μCi of sodium $^{123}$iodide in sodium hydroxide, together with 1 ml of 0.05M sodium phosphate buffer at pH 7.4. The mixture was incubated in the ice bath at 0° C. for 10 minutes, then decanted. Thin layer chromatography on Tech silica gel, using the same system as in section A, gave a product $R_f$ of 0.485.

By again repeating the procedure of section A above using sodium $^{131}$iodide, sodium $^{75}$bromide and sodium $^{77}$bromide, respectively, in place of sodium $^{125}$iodide, the 3-$^{131}$iodo, 3-$^{75}$bromo and 3-$^{77}$bromo derivatives of N-[L-1-carboxy-2-(4-hydroxyphenyl)ethyl]-Ala-L-Pro, respectively, are obtained.

EXAMPLE II

A female albino rabbit, weighing 4.5 kg, was anesthetized with approximately 30 mg/kg of rabbit weight of Nembutal pentobarbital, 1:1 dilution Nembutal:saline, (concentration 50 mg/ml Nembutal) administered intravenously. The animal was then injected via a marginal ear vein, with 50 μCi of N-[L-1-carboxy-2-(4-hydroxy-3-$^{123}$iodophenyl)ethyl]-Ala-L-Pro. FIG. 1, a representation of the scan taken 5 minutes after injection at St. Vincent's Hospital, New York, N.Y., using a standard ANGER camera (Searle) and an analog Polaroid picture, clerly shows the bodily organs of the rabbit 1 imaged—the heart 2, the kidneys 3 and the urinary bladder 4.

EXAMPLE III

A male rabbit, weighing 2.55 kg, was anesthetized with Nembutal, 30 mg/kg of rabbit weight, 1:1 dilution Nembutal:saline (concentration 50 mg/ml Nembutal) administered intravenously. The animal was then injected, via a marginal ear artery, with 324 μCi of N-[L-1-carboxy-2-(4-hydroxy-3-$^{125}$iodophenyl)ethyl]-Ala-L-Pro. Twenty percent window was used for the scanner, a standard ANGER camera (Searle), and the image was obtained by an analog Polaroid picture.

Figure 2:
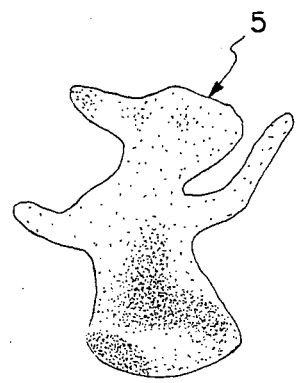
FIG. 2 is a representation of an anterior-posterior view of the scan described in Example III.

FIG. 2, a representation of the thus-obtained testicular image 5 of the rabbit, was obtained 8 minutes post injection. The animal was sacrificed approximately 40 minutes post injection, at which point the image was still maintained.

At necropsy, individual organs were taken and measured for radioactivity using a gamma counter. The kidneys, lungs, heart and stomach had the highest concentrations.

It will be obvious to those skilled in the art that other changes can be made in carrying out the present invention without departing from the spirit and scope thereof as defined in the appended claims.

We claim:

1. A radiolabeled angiotensin converting enzyme (ACE) inhibitor having the general formula:

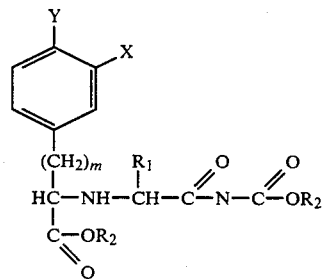

wherein
X is a radiolabeling substituent,
Y is hydroxy, alkoxy containing from 1 to 6 carbon atoms, phenoxy, benzyloxy or amino,
$R_1$ is hydrogen or methyl,
$R_2$ is hydrogen, an ester moiety hydrolyzable under mammalian in vivo conditions or an ionically bonded anion of a physiologically acceptable non-toxic salt, and
m is an integer of from 1 to 6.

2. A radiolabeled ACE inhibitor as described in claim 1 wherein X is a radiolabeling halogen substituent.

3. A radiolabeled ACE inhibitor as described in claim 2 wherein X is $^{123}$I, $^{125}$I, $^{131}$I, $^{75}$Br or $^{77}$Br.

4. A radiolabeled ACE inhibitor as described in claim 2 wherein X is a radiolabeling iodine substituent.

5. A radiolabeled ACE inhibitor having the general formula:

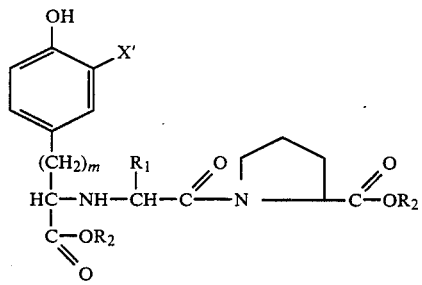

wherein X' is a radiolabeling iodine substituent, $R_1$ is hydrogen or methyl, $R_2$ is hydrogen, an ester moiety hydrolyzable under mammalian in vivo conditions or an ionically bonded anion of a physiologically acceptable non-toxic salt, and m is an integer of from 1 to 6.

6. N-[L-1-carboxy-2-(4-hydroxy-3-$^{123}$iodophenyl)ethyl]-Ala-L-Pro.

7. N-[L-1-carboxy-2-(4-hydroxy-3-$^{125}$iodophenyl)ethyl]-Ala-L-Pro.

8. N-[L-1-carboxy-2-(4-hydroxy-3-$^{131}$iodophenyl)ethyl]-Ala-L-Pro.

9. A method of radioimaging a mammalian site which comprises administering into a blood vessel in the mammal a dose of from about 0.01 mg to about 15 mg, per kilogram of body weight, of a radiolabeled angiotensin converting enzyme (ACE) inhibitor as described in claim 1, and then scanning the mammal to produce an image of the site.

10. A method as described in claim 9 wherein said mammal is a human being, said radiolabeled ACE inhibitor is N-[L-1-carboxy-2-(4-hydroxy-3-$^{123}$iodophenyl)ethyl]-Ala-L-Pro or N-[L-1-carboxy-2-(4-hydroxy-3-$^{131}$iodophenyl)ethyl]-Ala-L-Pro, administered in a dose of from about 0.05 mg to about 5 mg per kilogram of body weight, and the total radioactivity from said dose is less than about 100 μCi.

* * * * *